(12) United States Patent
Imazono et al.

(10) Patent No.: US 8,983,032 B2
(45) Date of Patent: Mar. 17, 2015

(54) SPECTROSCOPIC APPARATUS

(71) Applicants: Japan Atomic Energy Agency, Ibaraki (JP); Jeol Ltd., Tokyo (JP); Shimadzu Corporation, Kyoto (JP); Tohoku University, Miyagi (JP)

(72) Inventors: Takashi Imazono, Kyoto (JP); Masato Koike, Kyoto (JP); Hideyuki Takahashi, Tokyo (JP); Hiroyuki Sasai, Kyoto (JP); Masami Terauchi, Miyagi (JP)

(73) Assignees: Japan Atomic Energy Agency, Ibaraki (JP); Jeol Ltd., Tokyo (JP); Shimadzu Corporation, Kyoto (JP); Tohoku University, Miyagi (JP)

( * ) Notice: Subject to any disclaimer, the term of this patent is extended or adjusted under 35 U.S.C. 154(b) by 170 days.

(21) Appl. No.: 13/856,834

(22) Filed: Apr. 4, 2013

(65) Prior Publication Data

US 2013/0266120 A1 Oct. 10, 2013

(30) Foreign Application Priority Data

Apr. 6, 2012 (JP) ................ 2012-087536

(51) Int. Cl.
*G21K 1/06* (2006.01)
*G01N 23/20* (2006.01)
(52) U.S. Cl.
CPC ......... *G21K 1/06* (2013.01); *G01N 23/20* (2013.01); *G21K 1/062* (2013.01)
USPC .......................................................... 378/85

(58) Field of Classification Search
USPC ..................... 378/70, 71, 79, 84, 85
See application file for complete search history.

(56) References Cited

U.S. PATENT DOCUMENTS

| | | | |
|---|---|---|---|
| 5,016,265 A | * | 5/1991 | Hoover ........................... 378/43 |
| 5,274,435 A | * | 12/1993 | Hettrick ......................... 356/328 |
| 7,003,075 B2 | * | 2/2006 | Miyake et al. .................. 378/82 |

FOREIGN PATENT DOCUMENTS

| | | |
|---|---|---|
| JP | H06-064207 B2 | 8/1994 |
| JP | 2006-133280 A | 5/2006 |
| JP | 2007-273477 A | 10/2007 |
| JP | 2009-300303 A | 12/2009 |

* cited by examiner

*Primary Examiner* — Irakli Kiknadze
(74) *Attorney, Agent, or Firm* — Paul F. Neils, Esq.; Edwards Neils PLLC

(57) ABSTRACT

To cover a wide wavelength bandwidth, a spectroscopic apparatus uses three varied line spacing concave diffraction gratings $G_1$ to $G_3$, the corresponding energy ranges for $G_1$, $G_2$, and $G_3$ being 50 to 200, 155 to 350, and 300 to 2200 eV, respectively. In the respective wavelength ranges, the diffraction conditions are satisfied. To provide a high throughput and a high resolution in the respective wavelength regions, the incident angles $\alpha_1$ to $\alpha_3$ for $G_1$ to $G_3$ measured from the normal line of the diffraction grating are specified to be $\alpha_1 < \alpha_2 < \alpha_3$. Presupposing the normal lines of all diffraction gratings are superposed upon a common normal line, in order to meet $\alpha_1 < \alpha_2 < \alpha_3$, the center positions $\Delta_1$ to $\Delta_3$ for $G_1$ to $G_3$ are set on the normal line (as $\Delta_1 < \Delta_2 < \Delta_3$). From $G_1$ to $G_3$, one diffraction grating can be selected.

6 Claims, 13 Drawing Sheets

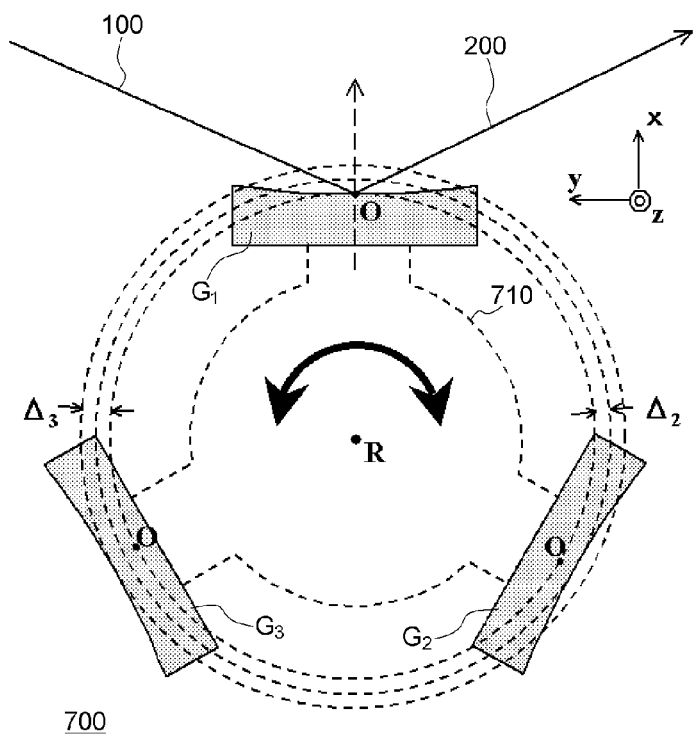
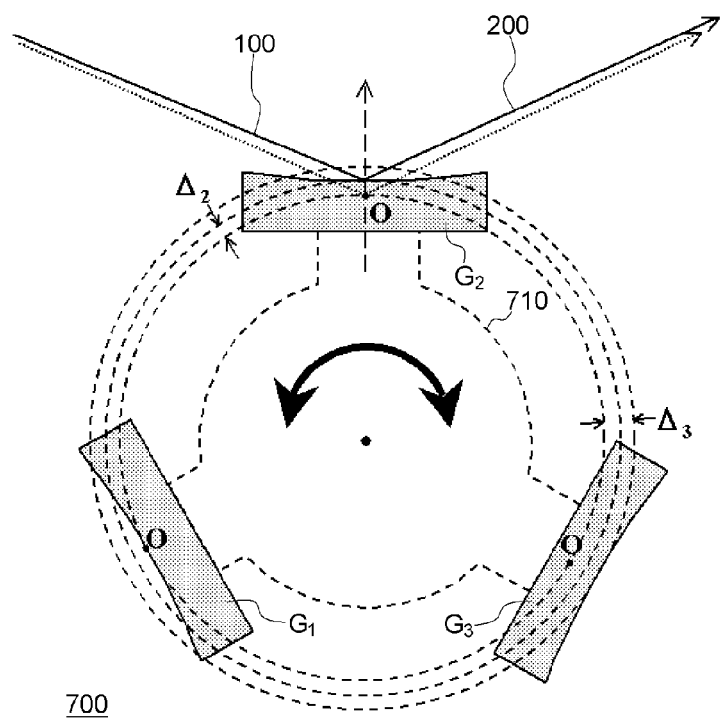
Fig.12

SPECTROSCOPIC APPARATUS

CROSS-REFERENCE TO RELATED APPLICATIONS AND PRIORITY CLAIMS

This present application claims the benefit of priority from Japanese Patent Application No. 2012-087536, which was filed Apr. 6, 2012, the contents of which are incorporated herein by reference in their entirety.

BACKGROUND OF THE INVENTION

1. Field of the Invention

The present invention relates to a spectroscopic apparatus which uses a varied line spacing diffraction grating.

2. Description of the Related Art

The spectroscopic apparatus which, from a non-monochromatic incident light, outputs monochromatic light having a desired wavelength has found widespread use in various physical experiments and measurements. As the spectroscopic apparatus which outputs light in the soft x-ray region, a spectroscopic apparatus using a diffraction grating (for example, a laminar-type diffraction grating having rectangular grooves) is known. In this case, with the spectroscopic apparatus using the diffraction grating, by selecting an incident angle or an exit angle (diffracted angle) with respect to the grating normal of the diffraction grating, a monochromatic ray having a desired wavelength can be obtained. Here, if a concave diffraction grating is used, image formation can be simultaneously performed in addition to spectral dispersion.

With such a diffraction grating for the soft x-ray region, the wavelength range (energy range) which can be obtained using one diffraction grating is limited, and in the range beyond this limit, the diffraction efficiency is greatly reduced or the resolution is greatly lowered. Therefore, a structure for the purpose of widening this range has been proposed. For example, in Patent Literature 1, there is disclosed a varied line spacing (VLS) diffraction grating which has widened this range by providing the lattice plane with a distribution of line spacings rather than a uniform line spacing. Further, Patent Literature 2 discloses a configuration in which the diffraction plane of the diffraction grating is divided into a plurality of regions, and in the respective regions, the range of wavelengths to be accommodated is optimized.

In case of a spectroscopic apparatus which uses a VLS concave diffraction grating for accommodating light in the soft x-ray region, the energy range in which a practicable diffraction efficiency and resolution can be maintained is 60 to 250 eV (20 to 5 nm wavelength) or so, assuming that, for example, the central value of the grating constant is set at $1/1200$ mm, and the incident angle (the angle between the grating normal and the incident ray) is at 87°. Since the image plane for a diffracted light by a VLS concave grating can be made flat, in the case where a two-dimensional detector, such as a charge coupled device (CCD), is used as a detector, the light in the relevant energy region can be simultaneously detected. This is a feature of the spectroscopic apparatus using a VLS concave grating. Further, assuming that the lattice constant is set at $1/2400$ mm, and the angle of incidence at 88.7°, the energy range of 250 to 1240 eV (5 to 1 nm wavelength) or so is obtained. Also in this case, since the image plane can be made flat, the light in the relevant energy region can be simultaneously detected. However, as a matter of fact, it is difficult to obtain a single VLS concave grating with both high diffraction efficiency and high resolution uniformly in the range of, for example, 60 to 1240 eV.

Therefore, in Patent Literature 3, for example, there is disclosed a technology which uses a plurality of VLS gratings by switching over among them. This technology employs translation or pivoting movement to switch over among the plurality of VLS gratings.

CITATION LIST

Patent Literature

Patent Literature 1: Japanese Unexamined Patent Application Publication No. 2006-133280
Patent Literature 2: Japanese Unexamined Patent Application Publication No. 2009-300303
Patent Literature 3: Japanese Unexamined Patent Application Publication No. 2007-273477

For a VLS concave grating, the parameters, such as the grating constant, the groove pattern (groove function), the groove shape, and the curvatures of the grating substrate, are determined such that a high diffraction efficiency and resolution can be obtained, in consideration of the desired energy range and the optical positional relationship of the diffraction grating (the position of the light source, the incident angle, the focal distance, and the like). In this case, if the range of wavelengths to be accommodated varies, an optimum optical positional relationship is also varied. This is because the relationship between the diffraction efficiency and the angle of incidence has a wavelength dependency. For example, in order to enhance the diffraction efficiency for light having a relatively high energy (short wavelength) in the soft x-ray region, it is required that the angle of incidence be close to 90°, as compared to that with a low energy (a long wavelength). Here, the angle of incidence is measured from the normal line of the diffraction grating.

Therefore, in the case where a plurality of VLS grating are used, being switched over among them, as disclosed in Patent Literature 3, it is necessary that the angle of incidence or the position of the image plane be adjusted for each VLS grating. In this case, such adjustment operation will become extremely complicated. Especially in the case where the energy range is wide, and a number of VLS gratings are to be used, this operation has become extremely complicated, and in addition, it has been difficult to obtain a high accuracy.

In other words, it has been difficult to obtain, with the use of a plurality of VLS gratings, a spectroscopic apparatus which is capable of covering a wide wavelength bandwidth.

The present invention has been made in view of such problems, and it is an object of the present invention to provide a solution to the problems.

SUMMARY OF THE INVENTION

In order to solve the above problems, the present invention provides the following configurations.

According to one aspect of the present invention, there is provided a spectroscopic apparatus, having a plurality of VLS gratings differing in range of wavelengths to be accommodated, one grating being selected from among the plurality of VLS gratings for obtaining a desired wavelength of output light, an incident ray emitted from a light source entering the one VLS grating, and a diffracted ray focusing onto an image surface common to all the VLS gratings, the spectroscopic apparatus including a selection means for selecting the one VLS grating to install it in a position where the incident ray is to be entered, wherein, in selecting the one grating from among the plurality of VLS gratings, the selection means treats the normal line passing through the center of the groove plane of the respective VLS gratings as one to be superposed upon a common normal line, and in case where the light source is on the upper side of the groove plane, selects the one VLS grating and installs it such that the smaller the value of the minimum wavelength to be accommodated, the higher the position at which the groove plane is set.

According to another aspect of the present invention, there is provided a spectroscopic apparatus, wherein the light source emits light having a wavelength in the range of 0.5 to 25 nm.

According to another aspect of the present invention, there is provided a spectroscopic apparatus, wherein the groove plane of the VLS grating is provided with a concave geometry.

According to another aspect of the present invention, there is provided a spectroscopic apparatus, wherein a lattice groove pattern in the VLS grating has been formed by using an aspherical wavefront holographic recording method.

According to another aspect of the present invention, there is provided a spectroscopic apparatus, wherein a multi-layer film has been formed on the groove plane in the VLS grating.

According to another aspect of the present invention, there is provided a spectroscopic apparatus, wherein the selection means selects the one VLS grating by translating or pivoting the plurality of VLS gratings to a position where the normal line passing through the center of the groove plane of the one VLS grating is superposed upon the common normal line.

The present invention is configured as above, whereby a spectroscopic apparatus can be obtained which allows a wide wavelength bandwidth to be covered with the use of a plurality of VLS gratings.

BRIEF DESCRIPTION OF THE DRAWINGS

FIG. 12 gives the configuration of a third example of the spectroscopic apparatus according to an embodiment of the present invention.

DETAILED DESCRIPTION OF THE PREFERRED EMBODIMENT

Figure 1:
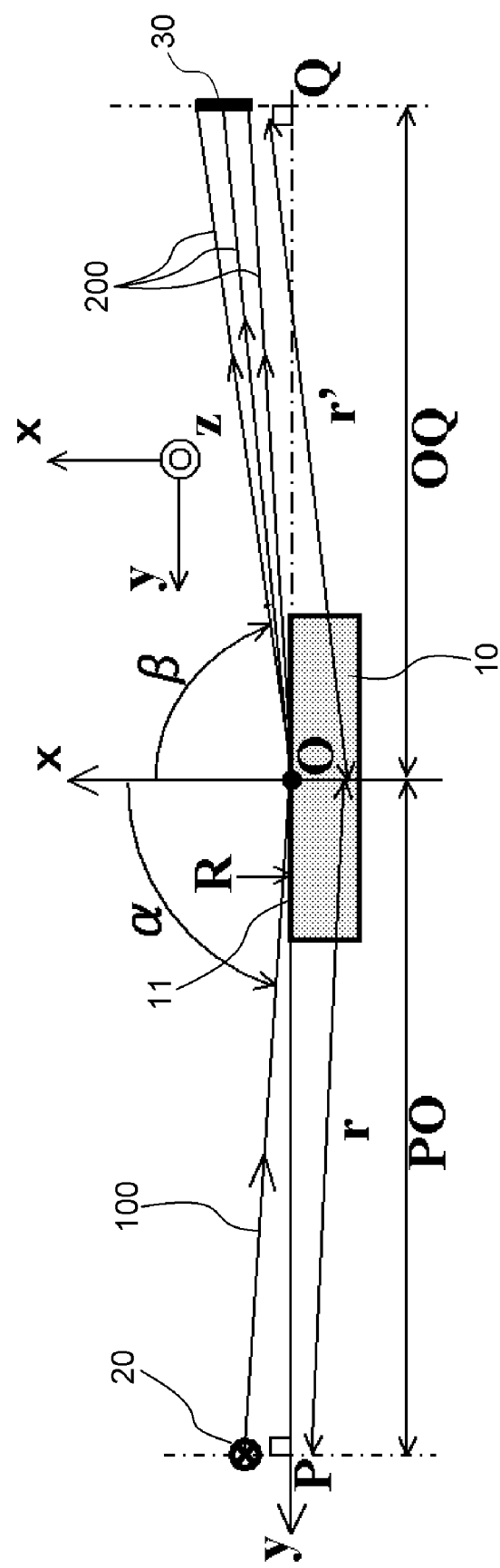
FIG. 1 is a figure illustrating a configuration in which a VLS concave diffraction grating is used.

Hereinafter, a spectroscopic apparatus according to an embodiment of the present invention will be described. With this spectroscopic apparatus, three types of VLS concave gratings are used, being switched over from one type to another. FIG. 1 is a figure illustrating a configuration in which a single VLS concave grating 10 is used in the spectroscopic apparatus. Herein, a section perpendicular to a groove plane 11 is shown, including a light source 20, an incident ray 100, and a diffracted ray 200. This VLS concave diffraction grating 10 diffracts or spectrally disperses a non-monochromatic ray (a soft x-ray) emitted from the light source (a point source) 20 to focus on an image surface 30 for respective energies (wavelengths). In other words, a diffracted monochromatic ray having a desired wavelength can be obtained on the image surface 30. The coordinate origin for the x-, y-, and z-axes is denoted as a letter O, and herein the origin O is equal to the center of the groove plane 11 (the diffraction grating center). The x-axis is a direction heading upward from the origin O, perpendicularly to the groove plane 11 in FIG. 1, this direction providing the direction of the normal line of the groove plane 11 at the diffraction grating center. The y-axis is a direction heading toward the side on which the light source 20 exists, perpendicularly to the x-axis at the origin O, within a plane (the surface of the paper in FIG. 1) which includes the x-axis, the incident ray 100, and the diffraction ray 200. Although not shown, the z-axis is a direction which is headed from the back side of the surface of the paper toward this side, perpendicularly to the surface of the paper, passing through the origin O (the right-handed coordinate system being used). In other words, the direction of the z-axis provides a direction perpendicular to the plane including the incident ray 100 directed toward the groove plane 11 and the diffraction ray 200 thereof.

The reference character r denotes the distance from the origin O to the light source 20 (the optical path length for the incident ray 100), and the reference character r' denotes the focal distance for the VLS concave grating 10, being equal to the optical path length for the diffracted ray 200. The incident angle α is defined as an angle formed by the incident ray 100 and the x-axis, and the diffracted angle (the exit angle) β is as an angle formed by the diffracted ray 200 and the x-axis, either of the angles α and β being assigned a positive one when measured in a counterclockwise direction. The point of intersection between a straight line extending from the light source 20 in parallel with the x axis (a perpendicular line to the y-axis) and the y-axis is denoted as the letter P, and the point of intersection between a straight line extending from the image surface 30 in parallel with the x-axis (a perpendicular line to the y-axis) and the y-axis is denoted as the letter Q.

Here is an explanation of the parameters used in the design of a VLS concave grating 10. The incident angle α, the diffracted angle β, the distance r to the light source 20, and the focal distance r' are determined by the positional relationship among the light source 20, the image plane 30, and this VLS concave grating 10. In the case where the radius of curvature of the concave surface (assuming that the center of curvature being located on the top side in FIG. 1) is R; the wavelength of the diffracted ray is λ; the order of diffraction is m; the effective grating constant is σ (the grating constant at the grating center); and as stated in Patent Literature 1, the projective coordinate of an nth groove on the y-axis is w, expressing the product of the groove function n (w) and σ as in Eq. (1), using the expansion coefficients $n_{20}$, $n_{30}$, and $n_{40}$ denoting varied line spacing grooves, will make Eq. (2) to Eq. (4) true.

$$n\sigma = w + n_{20}w^2 + n_{30}w^3 + n_{40}w^4 + \ldots \quad (1)$$

$$\frac{\cos^2\alpha}{r} + \frac{\cos^2\beta}{r'} - \frac{\cos\alpha + \cos\beta}{R} + 2n_{20}\frac{m\lambda}{\sigma} = 0 \quad (2)$$

$$\sin\alpha + \sin\beta = \frac{m\lambda}{\sigma} \quad (3)$$

$$r = \frac{PO}{\cos\alpha}, r' = \frac{OQ}{\cos\beta} \quad (4)$$

From Eq. (3) and Eq. (4), the r and r' can be given as a function of the wavelength λ. Accordingly, as a matter of fact, it is impossible to set the R and $n_{20}$ such that, with the α, β, r, and r', which are parameters defining the optical positional relationship, being specified to be constant, the above relationship is satisfied at all the wavelengths to be accommodated. Therefore, the σ, n(w), R, and the like, are set such that any one of these parameters is held to within the narrowest possible range for the range of wavelengths as an object. The above positional relationship is determined by the $n_{20}$ among the coefficients in Eq. (1). The $n_{30}$, $n_{40}$, and the like have no significant effect on the focal point, affecting greatly the coma and higher aberrations, however, a discussion about this point will be made later, and here the $n_{30}$ and $n_{40}$ will be neglected.

Here, it is clear that the wider the range of wavelengths to be accommodated, the more difficult the above setting will be. Therefore, herein, a plurality of VLS concave gratings ($G_1$ to $G_n$) are used, each having the range of wavelengths to be accommodated that is different from that for another ($G_1$: wavelength $\lambda_{12}$ to $\lambda_{11}$, $G_2$: $\lambda_{22}$ to $\lambda_{21}$, ... $G_n$: $\lambda_{n2}$ to $\lambda_{n1}$; where $\lambda_{11} > \lambda_{12}$, $\lambda_{21} > \lambda_{22}$, ..., $\lambda_{n1} > \lambda_{n2}$; and for the respective central wavelengths, $(\lambda_{11}+\lambda_{12})/2 > (\lambda_{21}+\lambda_{22})/2 > \ldots > (\lambda_{n1}+\lambda_{n2})/2)$. In other words, the greater the value of k in $G_k$, the higher the value of the maximum energy (the smaller the value of the minimum wavelength) to be accommodated by $G_k$ will be. In this case, the R and the $n_{20}$ may be set for each of the $G_1$ to $G_n$. In this case, it is obvious that the design can be made easily, as compared to the case where a single VLS concave grating is used. The respective VLS concave gratings may be designed such that the above relationship is satisfied only for the respective ranges of wavelengths to be accommodated.

In the case where the $G_1$ to $G_n$ are used, being switched over among them, making the optical positional relationship (α, β, r, and r') common to all of them will render the switchover operation extremely easy and enhance the reliability thereof. Therefore, it is desirable that α, β, r, and r' be common to all of the $G_1$ to $G_n$. However, as a matter of fact, this is also difficult. This is because the reflectivity especially in the soft x-ray region is high only in a narrow range where the angle of incidence is close to 90°, and if the wavelength is short (the energy is high), the reflectivity is remarkably lowered. The diffraction efficiency of a VLS concave grating greatly depends upon the reflectivity of the material constituting the groove plane surface thereof. In other words, the diffraction efficiency also shows the same tendency as this reflectivity.

Further, the output (the intensity of the diffracted light measured by the spectroscopic apparatus will not be determined simply by the magnitude of the diffraction efficiency alone. In the above example, the light source 20 is used as a point source, and for simplicity, only the diffraction at the diffraction grating center has been described, however, actually, the light emitted from the light source 20 is irradiated onto substantially the entire surface of the groove plane of the diffraction grating, and diffracted. Especially for a VLS concave grating, the setting is made such that this light is concentrated on the image plane 30. Therefore, the intensity of the light obtained on the image plane 30 is increased in the case where the angle of view when the VLS concave grating is viewed from the light source 20 is large. In the configuration shown in FIG. 1, the angle of view is at a maximum when α=0°, and zero when α=90°, being in proportion to cos α. Thus, as an appropriate factor to obtain output light having a high intensity, the product of the reflectivity and the angle of view can be adopted.

Figure 2:
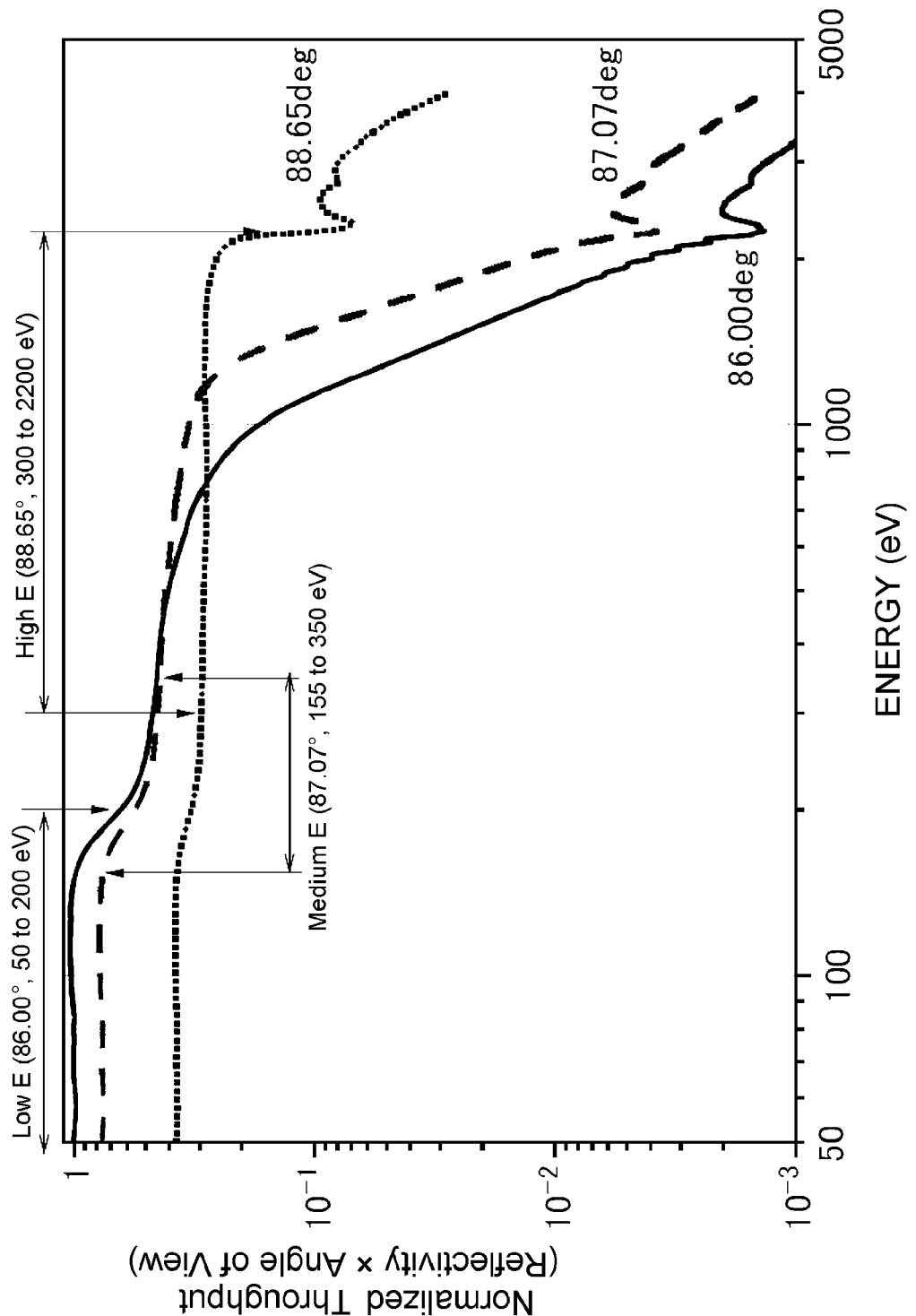
FIG. 2 gives a result of calculating the energy dependency of the throughput of a spectroscopic apparatus for the soft x-ray region, using the angle of incidence as a parameter.

FIG. 2 gives a result of calculating the energy dependency of the product of the reflectivity and the angle of view (which is defined as the throughput) for gold to be used as the material constituting the surface of the VLS concave grating for three different angles of reflection (corresponding to the values of α in FIG. 1, i.e., 86.00°, 87.07°, and 88.65°). From this result, it can be seen that, when the value of α is the smallest (most deviates from 90°), a high throughput is obtained at a low energy (long wavelength), however, the throughput is greatly reduced on the high energy (short wavelength) side. On the other hand, when the value of α is the closest to 90°, the energy dependency of the throughput is lowered, however, the throughput is low as a whole. However, if the discussion is limited to the high energy side alone, the throughput is greatly improved as compared to when the value of α is smaller.

This result reveals that, in the case where a plurality of VLS concave gratings $G_1$ to $G_n$ are to be used, being switched over among them, providing the VLS concave grating $G_1$ for low energy with the smallest value of α awhile providing the VLS concave grating $G_n$ for high energy with a value of α which is the closest to 90° is effective to enhance the throughput. In other words, if the values of α corresponding to the $G_1$ to $G_n$ are $\alpha_1$ to $\alpha_n$, it is preferable to provide a configuration in which the value of α is varied such that $\alpha_1 \leq \alpha_2 \leq \ldots \leq \alpha_n < 90°$, rather than to provide a configuration in which the value of α is constant.

Thus, in the preferable configuration, since the value of α varies depending upon each particular VLS concave grating, fixing the light source 20 and the image plane 30 in FIG. 1 would require providing each particular VLS concave grating with a different installation position. From the magnitude correlation of $\alpha_1$ to $\alpha_n$, it will be effective that, when the diffraction grating center for $G_1$ is set at a position of x=0 (the origin O), the respective diffraction grating centers for $G_2$ and the subsequent are sequentially moved toward the direction of x>0. In other words, assuming that the x-coordinate for the diffraction grating center providing an angle of incidence $\alpha_k$ corresponding to $G_k$ is $\Delta_k$, since it holds that $\alpha_1 \leq \alpha_2 \leq \ldots \leq \alpha_k \leq \ldots \leq \alpha_n$, the relationship $\Delta_1 \leq \Delta_2 \leq \ldots \leq \Delta_k \leq \ldots \leq \Delta_n$ holds, and thus even if the light source 20 and the image plane 30 are fixed, a spectroscopic apparatus can be obtained which allows monochromatic light to be measured over a wide wavelength range with a high output and a high resolution, using $G_1$ to $G_n$ which are each set for an optimum angle of incidence.

Hereafter, a specific configuration of a spectroscopic apparatus providing an embodiment of the present invention will be described. Here, it is assumed that three types of (n=3) VLS concave diffraction gratings, $G_1$ to $G_3$, are used, the range of energies to be accommodated by $G_1$ being 50 to 200 eV ($\lambda_{11}$=24.7 nm, $\lambda_{12}$=6.2 nm wavelength), the range of energies to be accommodated by $G_2$ being 155 to 350 eV ($\lambda_{21}$=8.0 nm, $\lambda_{22}$=3.54 nm), and the range of energies to be accommodated by $G_3$ being 300 to 2200 eV ($\lambda_{31}$=4.133 nm, $\lambda_{32}$=0.564 nm). Table 1 gives the specifications designed for $G_1$ to $G_3$ such that the above diffraction requirements are satisfied in the respective ranges of wavelengths. Here, as described above, in order to allow $G_1$ to $G_3$ to provide a high output and a high resolution in the respective wavelength regions, the angles of incidence $\alpha_1$ to $\alpha_3$ for $G_1$ to $G_3$ that are measured from the normal line direction to the diffraction grating are specified so as to be $\alpha_1 < \alpha_2 < \alpha_3$. In addition, it is specified that PO=239.69 mm and OQ=233.50 mm. For the values of $\Delta$ corresponding to $\alpha_1$ to $\alpha_3$, it is specified that $\Delta_1 < \Delta_2 < \Delta_3$, and these are set as given in Table 1, for example.

TABLE 1

|  | Diffraction grating | | |
| --- | --- | --- | --- |
|  | Low energy (G1: Low E) | Medium energy (G2: Medium E) | High energy (G3: High E) |
| Energy Range (eV) | 50~200 | 155~350 | 300~2200 |
| Wavelength Range (nm) | 24.7~6.20 | 8.00~3.54 | 4.133~0.564 |
| R (mm) | 3960 | 5606 | 13800 |
| r (mm) | 237.27 | 237 | 236.76 |
| α (°) | 86.00 ($\alpha_1$) | 87.07 ($\alpha_2$) | 88.65 ($\alpha_3$) |
| 1/σ (mm$^{-1}$) | 1200 | 1200 | 2400 |
| $n_{20}$ (mm$^{-1}$) | $-3.396 \times 10^{-3}$ | $-3.523 \times 10^{-3}$ | $-3.816 \times 10^{-3}$ |
| $n_{30}$ (mm$^{-2}$) | $1.353 \times 10^{-5}$ | $1.373 \times 10^{-5}$ | $1.535 \times 10^{-5}$ |
| $n_{40}$ (mm$^{-3}$) | $-5.102 \times 10^{-8}$ | $-7.353 \times 10^{-8}$ | $-8.707 \times 10^{-8}$ |
| Δ (mm) | 0 ($\Delta_1$) | 4.44 ($\Delta_2$) | 10.97 ($\Delta_3$) |

Figure 3:
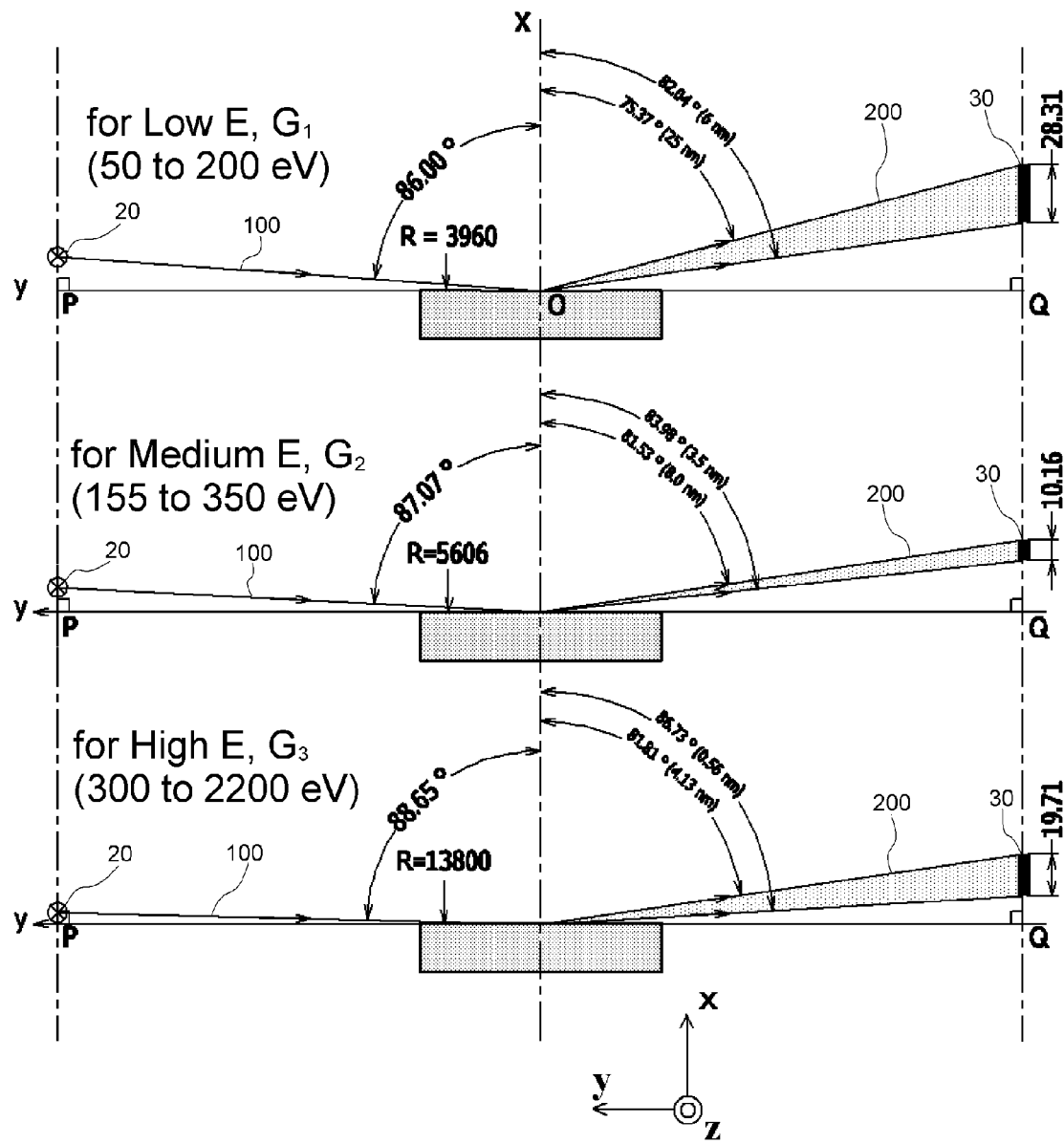
FIG. 3 is a figure illustrating the positional relationship among the light source, the incident ray, the diffracted ray, and the image plane for three types of VLS concave gratings.
Figure 4:
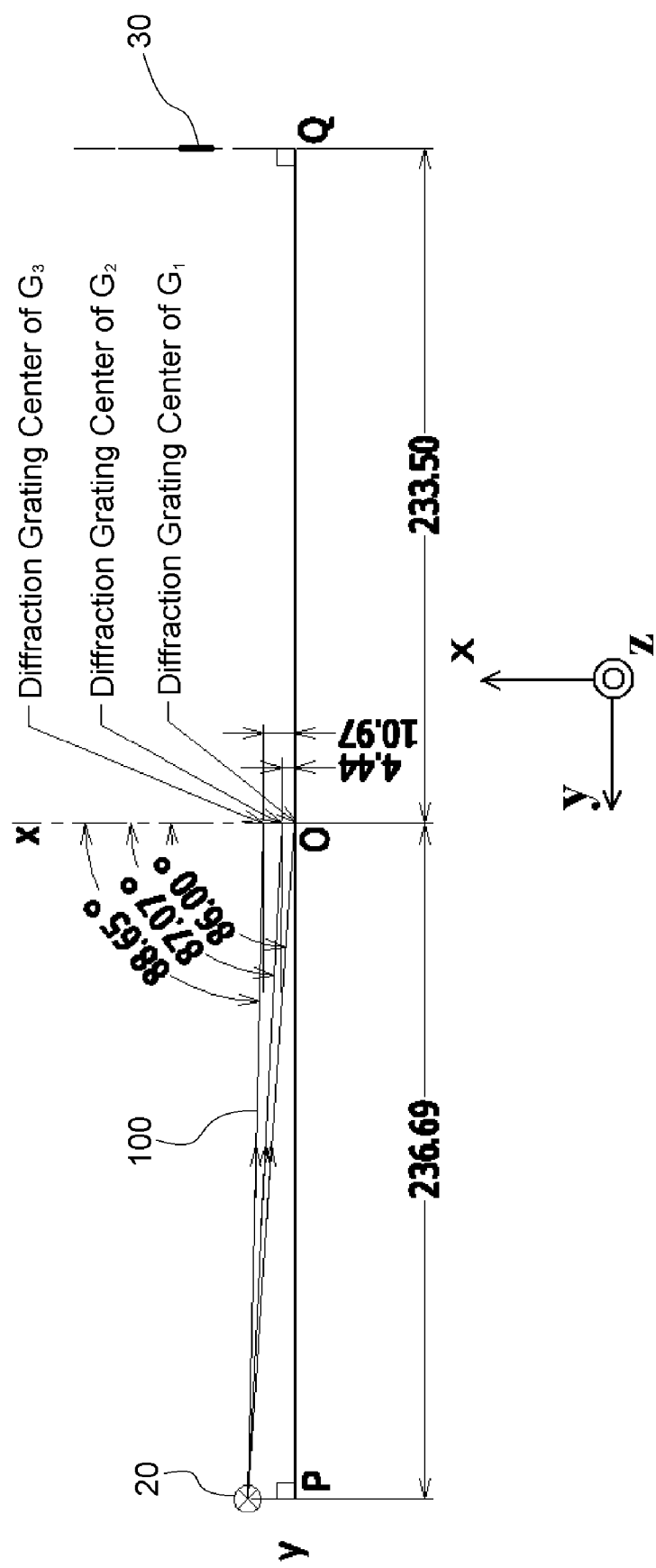
FIG. 4 is a figure in which the figures showing the positional relationship among the light source, the incident ray, the diffracted ray, and the image plane for three types of VLS concave gratings are superposed one upon another with the offset Δ of the center position of each of the diffraction grating in the x-axis direction being taken into account.

FIG. 3 illustrates the conditions of the light source 20, the incident ray 100, the diffracted ray 200, and the image plane 30 for $G_1$ to $G_3$. FIG. 4 is a figure illustrating a configuration in which $G_1$ to $G_3$ are superposed one upon another in consideration of $\Delta_1$ to $\Delta_3$ such that the positions of the light source 20 in FIG. 3 coincide with one another. At this time, the grating center of $G_1$ is set at the lowest position, while the grating center of $G_3$ is at the highest position (providing a relationship of $\Delta_1 < \Delta_2 < \Delta_3$). By doing this, one diffraction grating can be relatively conveniently selected as appropriate from among $G_1$ to $G_3$, whereby a spectroscopic apparatus which covers a wide wavelength bandwidth can be configured. In other words, the spectroscopic apparatus according to the embodiment of the present invention is configured such that, in switching over among $G_1$ to $G_3$, $\Delta_1$ to $\Delta_3$ can be utilized for switchover among the angles of incidence corresponding to $G_1$ to $G_3$.

Figure 5:
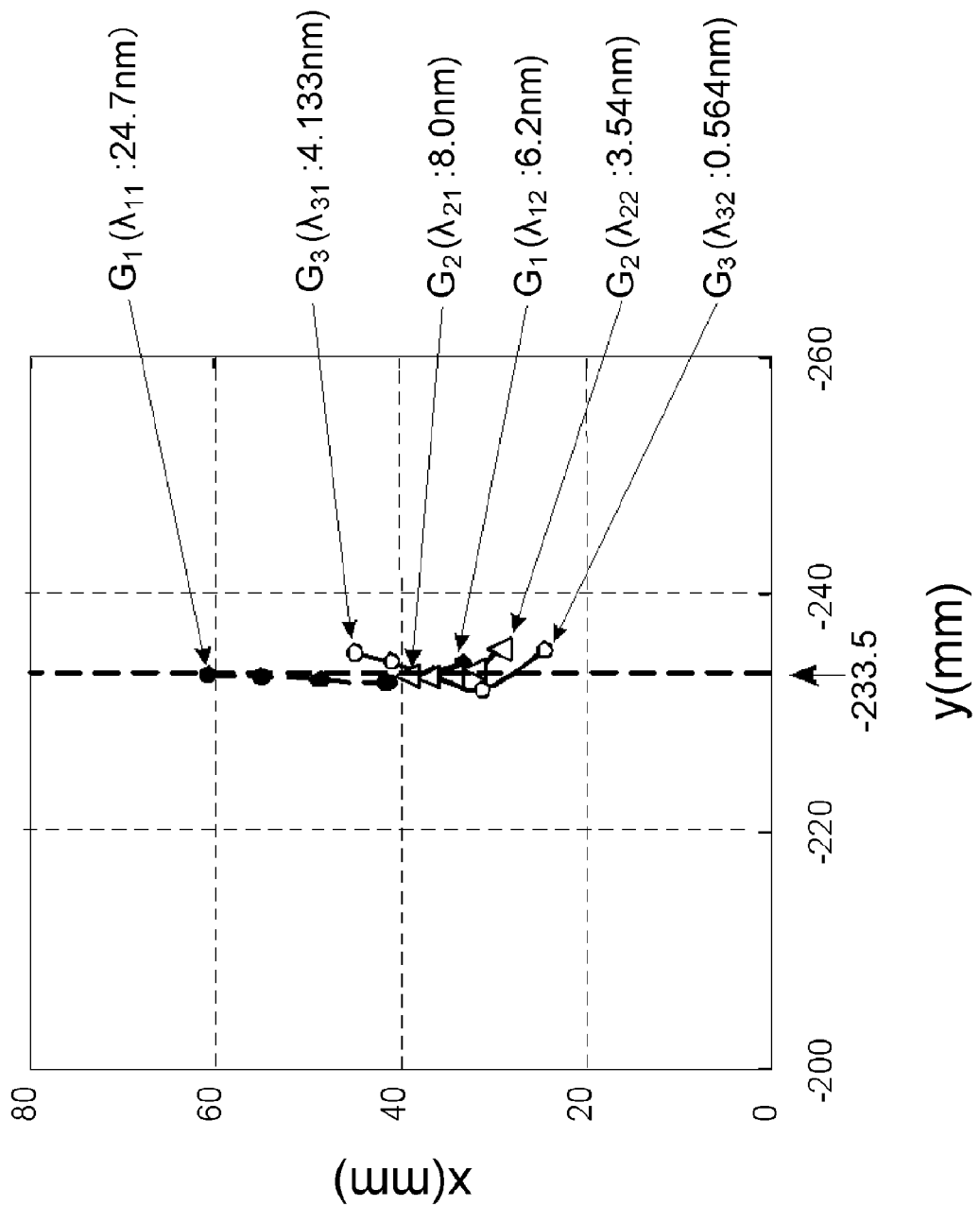
FIG. 5 is a figure illustrating a distribution of focal points in the spectroscopic apparatus according to an embodiment of the present invention.

As described above, also in the case where the configuration as shown in FIG. 4 is used, it will actually not occur that the focal points for the diffracted ray 200 are completely converged at a single point. FIG. 5 depicts the result of calculating a distribution of such focal points when viewed from the same direction as in FIG. 4. y=−233.5 mm provides the image plane. From this result, it can be confirmed that, with the configuration using $G_1$ to $G_3$ as shown in FIG. 4, the focal points calculated by Eq. (2) are kept within a range of <5 mm in the y-axis direction (the dispersion direction) relating to the image formation properties in a wide range of energies of 50 to 2200 eV (24.7 nm to 0.564 nm wavelength). In the x-axis direction, the focal points are held to within a range as wide as the length of the light receiving surface of a commercially available two-dimensional detector (approx. 25 mm). Therefore, even if a plurality of VLS concave gratings are used in order to cover a wide energy bandwidth, a spectroscopic apparatus having good image formation properties can be obtained.

In the above example, with only the coefficient $n_{20}$ in Eq. (1) being taken into account, a distribution of positions of the focal point has been indicated. Among the coefficients in Eq. (1), $n_{20}$ is a parameter relating to the focal point, and it has been indicated that, with the above configuration, the focal point can be kept substantially fixed. Contrarily to this, $n_{30}$ and $n_{40}$ are parameters relating to the higher aberrations. On the other hand, in forming the grooves in the above VLS concave grating, an aspherical wavefront holographic recording method, for example, is used. In this case, since the interference of light is utilized to form grating grooves, it is impossible to separately set the $n_{20}$, $n_{30}$, and $n_{40}$. Therefore, the $n_{20}$ is set so as to be a predetermined value, and under this condition, the $n_{30}$ and $n_{40}$ are set to be as appropriate as possible. Accordingly, actually, it is important to make evaluation including the effect of the aberrations as well.

Hereinafter, the result in the case where the aspherical wavefront holographic recording method is used to manufacture the above $G_1$ to $G_3$ will be explained. An aspherical wavefront holographic recording method is disclosed in, for example, Japanese Examined Patent Application Publication No. Hei 6-64207. With this manufacturing method, the monochromatic spherical wavefront(s) emitted from two point sources are reflected at both spherical mirrors or only either wavefront is reflected at a spherical mirror to interfere with each other on a photoresist coated on a grating substrate, thereby forming interference fringes. The configuration and arrangement of the light source and the spherical mirror are adjusted such that the pattern of the interference fringes provides a desired effective grating constant and groove pattern (VLS grooves). After the recording, the photoresist is developed for patterning it, and the substrate is etched using the pattern of photoresist as a mask to thereby form a desired groove geometry on the substrate surface. A diffraction grating in which grooves are ruled on the substrate itself after being etched is called a master diffraction grating, and replica diffraction gratings having the same groove spacing and groove geometry as those of the master diffraction grating are replicated based on the master grating after the several processing.

Figure 6:
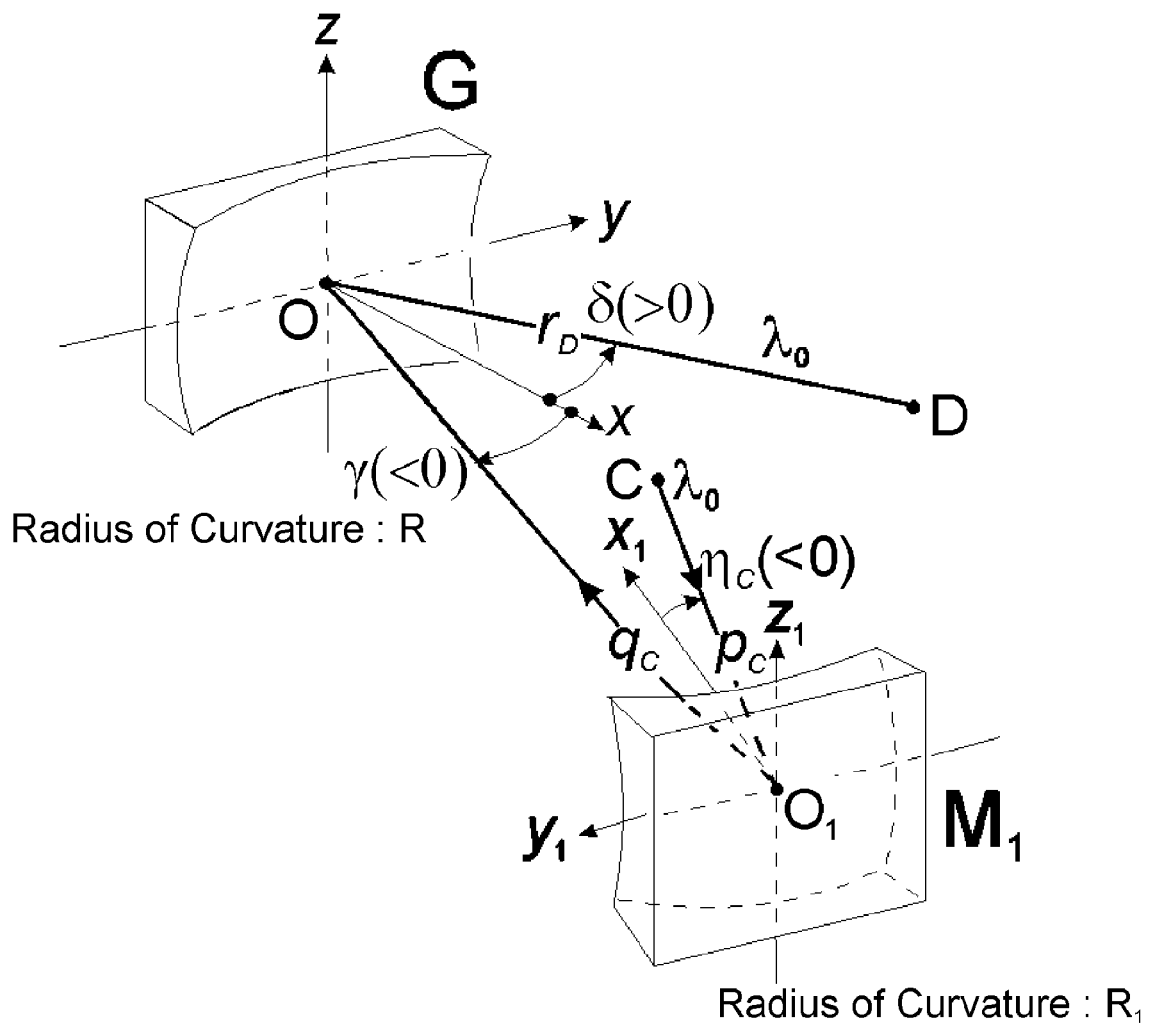
FIG. 6 is a figure illustrating a configuration (a first example) for use in forming a VLS pattern by an aspherical wavefront holographic recording method.
Figure 7:
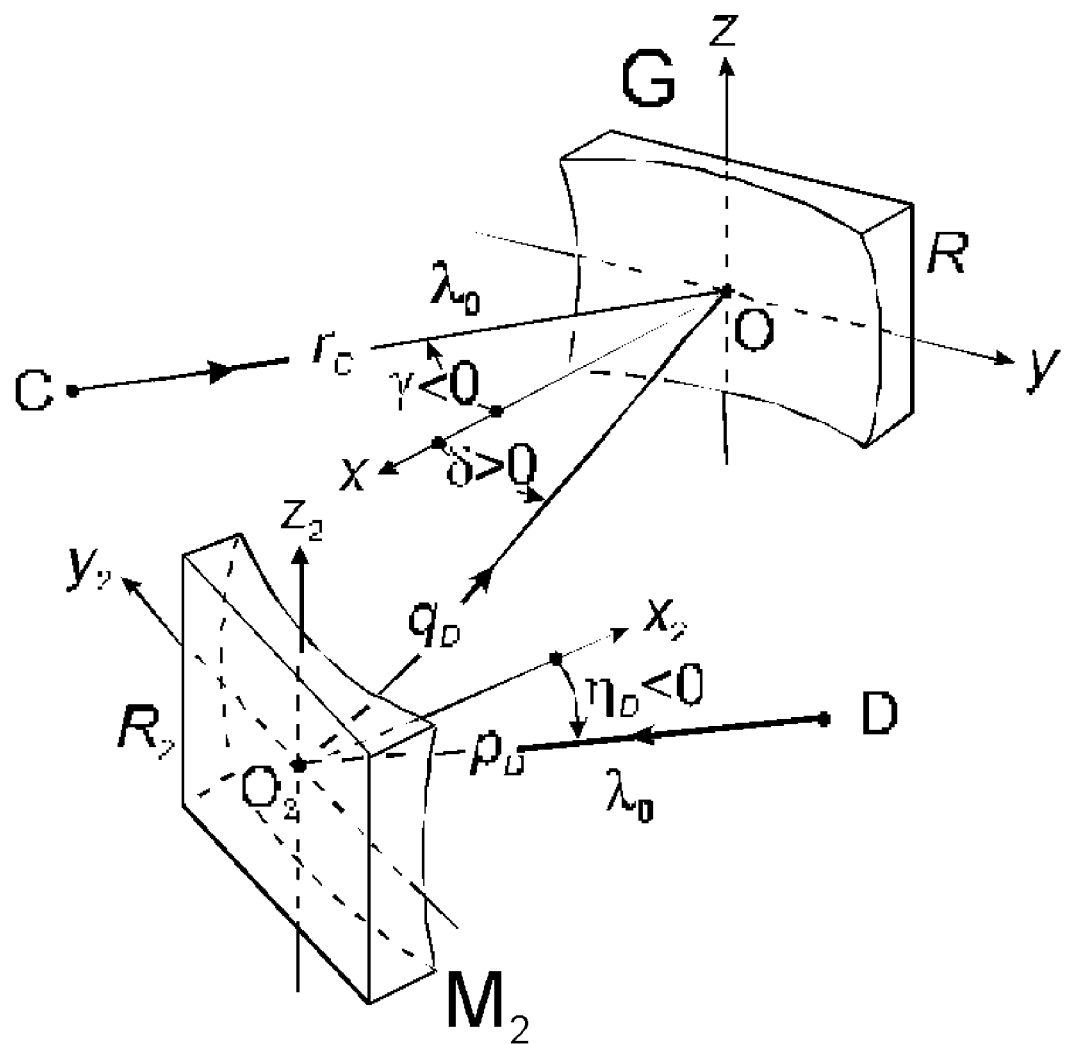
FIG. 7 is a figure illustrating a configuration (a second example) for use in forming a VLS pattern by an aspherical wavefront holographic recording method.

FIGS. 6 and 7 are figures illustrating two different configurations for use in implementing the aspherical wavefront holographic recording method, the reference characters C and D denoting a laser point source, the $M_1$ and $M_2$ spherical mirrors having the radius of curvature of $R_1$, $R_2$, respectively, and the G here an grating substrate on which interference fringes are to be patterned.

With the wavelength of the monochromatic light emitted from the laser light sources C and D being specified to be 441.6 nm, and the parameters in FIGS. 6 and 7 being as specified in Table 2, $G_1$ to $G_3$ were manufactured. In manufacturing $G_1$, the configuration as shown in FIG. 6 was used, while, in manufacturing $G_2$ and $G_3$, the configuration as shown in FIG. 7 was used.

TABLE 2

| | Diffraction grating | | |
|---|---|---|---|
| | Low energy (G1: Low E) | Medium energy (G2: Medium E) | High energy (G3: High E) |
| $\lambda_\alpha$ (nm) | 441.6 | 441.6 | 441.6 |
| $\gamma$ (°) | −8.412 | −57.722 | −62 |
| $\delta$ (°) | 22.559 | −18.394 | 10.189 |
| $R_1$ (mm) | 599.13 | — | — |
| $R_2$ (mm) | — | 599.13 | 400 |
| $p_C$ (mm) | 347.839 | 1890.99 | 2056.959 |
| $p_D$ (mm) | 583.948 | 599.13 | 830.025 |
| $q_C$ (mm) | 425 | — | — |
| $q_D$ (mm) | — | 599.13 | 301.284 |
| $\eta_C$ (°) | −33.508 | — | — |
| $\eta_D$ (°) | — | 49.162 | 41.25 |

Figure 8:
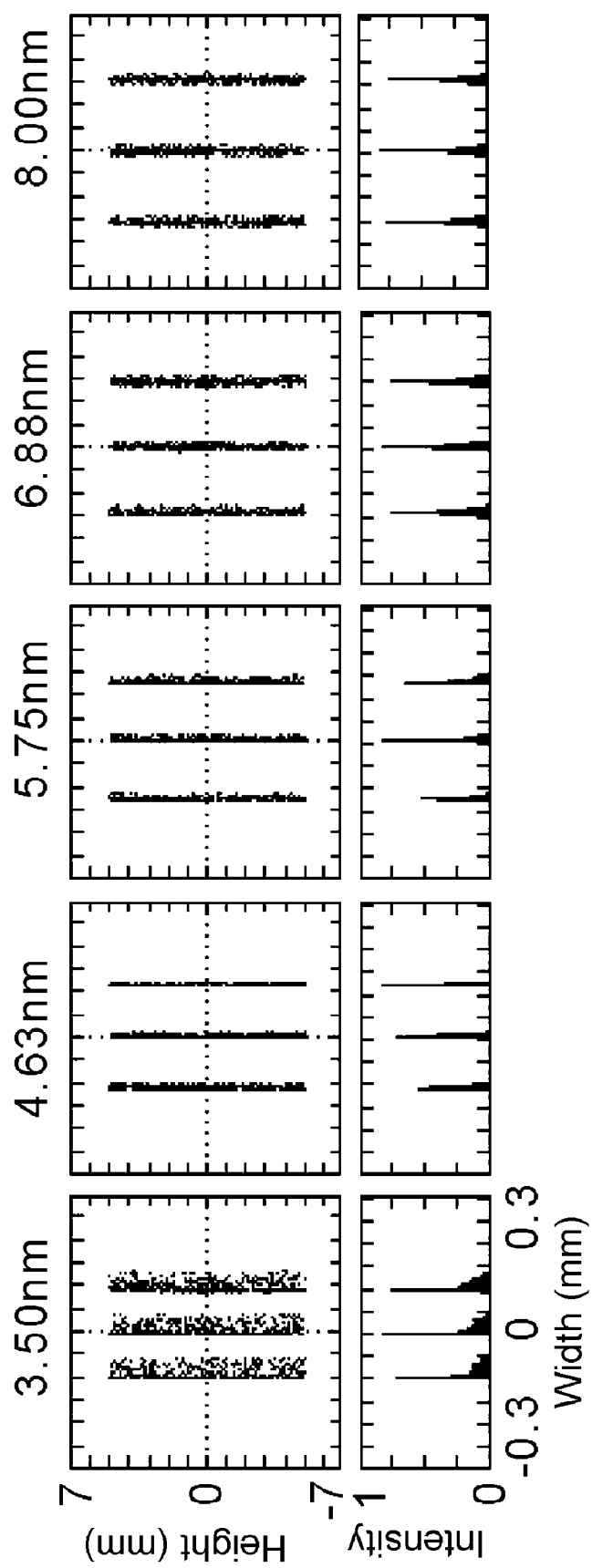
FIG. 8 gives an example of the image formation characteristics of a VLS concave grating for use in the spectroscopic apparatus according to an embodiment of the present invention.

FIG. 8 illustrates the result of examination of the image formation properties of $G_2$ for five different central wavelengths (3.50 nm, 4.63 nm, 5.75 nm, 6.88 nm, and 8.00 nm). The size of the diffraction grating surface was specified to be 50 mm in the y-axis direction and 30 mm in the z-axis direction. In FIG. 8, the figures at top correspond to the above respective central wavelengths $\lambda$, giving spot diagrams for the diffracted rays having subsidiary wavelengths of $\lambda_\pm=\lambda\pm\lambda/100$ (corresponding to a resolution of $\lambda/\Delta\lambda=100$), while the figures at bottom showing intensity distributions. From this result, the aberration causes the spectral image for the respective wavelengths to be expanded in the z-axis direction by approx. 60 mm. However, a commercially available two-dimensional detector, such as a CCD, is practicably capable of receiving light and detecting a spectral image up to approx. 10 mm in height. On the basis of this fact, if the detection range is restricted to ±5 mm (a height of 10 mm), the resolutions $\lambda/\Delta\lambda$ which can be obtained are 285 ($\lambda$=3.50 nm), 1463 ($\lambda$=4.63 nm), 1182 ($\lambda$=5.75 nm), 982 ($\lambda$=6.88 nm), and 1132 ($\lambda$=8.00 nm).

The fact that the resolution ($\lambda/\Delta\lambda=285$) at $\lambda$=3.50 nm is sufficiently high and practicable, however, it is inferior to those at the other wavelengths is attributable to that, in FIG. 5, the focusing position by Eq. (2) for $G_2$ ($\lambda_{22}$=3.54 nm) slightly deviates from the defined image formation surface (y=−233.5 mm). On the other hand, in the relevant wavelength region, $G_3$ with which the range of wavelengths to be accommodated is partially overlapped with that for $G_2$ may be used. In that case, the use of $G_3$ will provide a higher resolution than the use of $G_2$. However, as shown in FIG. 2, the throughput for $G_3$ is lower than that for $G_2$. Therefore, when the throughput is requisite, $G_2$ may be used, being switched over from $G_3$, as appropriate, while the resolution is requisite, $G_3$ may be used, being switched over from $G_2$, as appropriate, depending upon the application. Thus, by partially overlapping the ranges of wavelengths to be accommodated for $G_1$ to $G_n$, a configuration can be provided which allows the VLS concave grating to be selected in accordance with the application.

From the result as described above, it can be seen that, even in consideration of the aberrations are not fully corrected in the VLS concave grating actually manufactured, the above spectroscopic apparatus allows monochromatic light to be taken out at a high output and a high resolution in a wide wavelength range.

Next, a configuration of a spectroscopic apparatus with which $G_1$ to $G_3$ are used, being actually switched over among them, will be explained. With this spectroscopic apparatus, a selection means is used which selects one grating from among a plurality of VLS concave gratings, and installs it in a position where an incident ray is to be irradiated, and a diffracted ray (exit ray) is to be taken out. With this configuration, the normal line passing through the center of the groove plane of the respective VLS concave gratings is treated as one which is to be superposed upon a common normal line (the x-axis in FIG. 1). However, the level of the center of the groove plane of the respective VLS gratings in the direction of the x axis varies. This level is set in such a manner that the greater the value of the maximum wavelength to be accommodated by the VLS concave grating, the lower the level, and the smaller the value of the maximum wavelength to be accommodated by the varied space concave diffraction grating, the higher the level will be.

Figure 9:
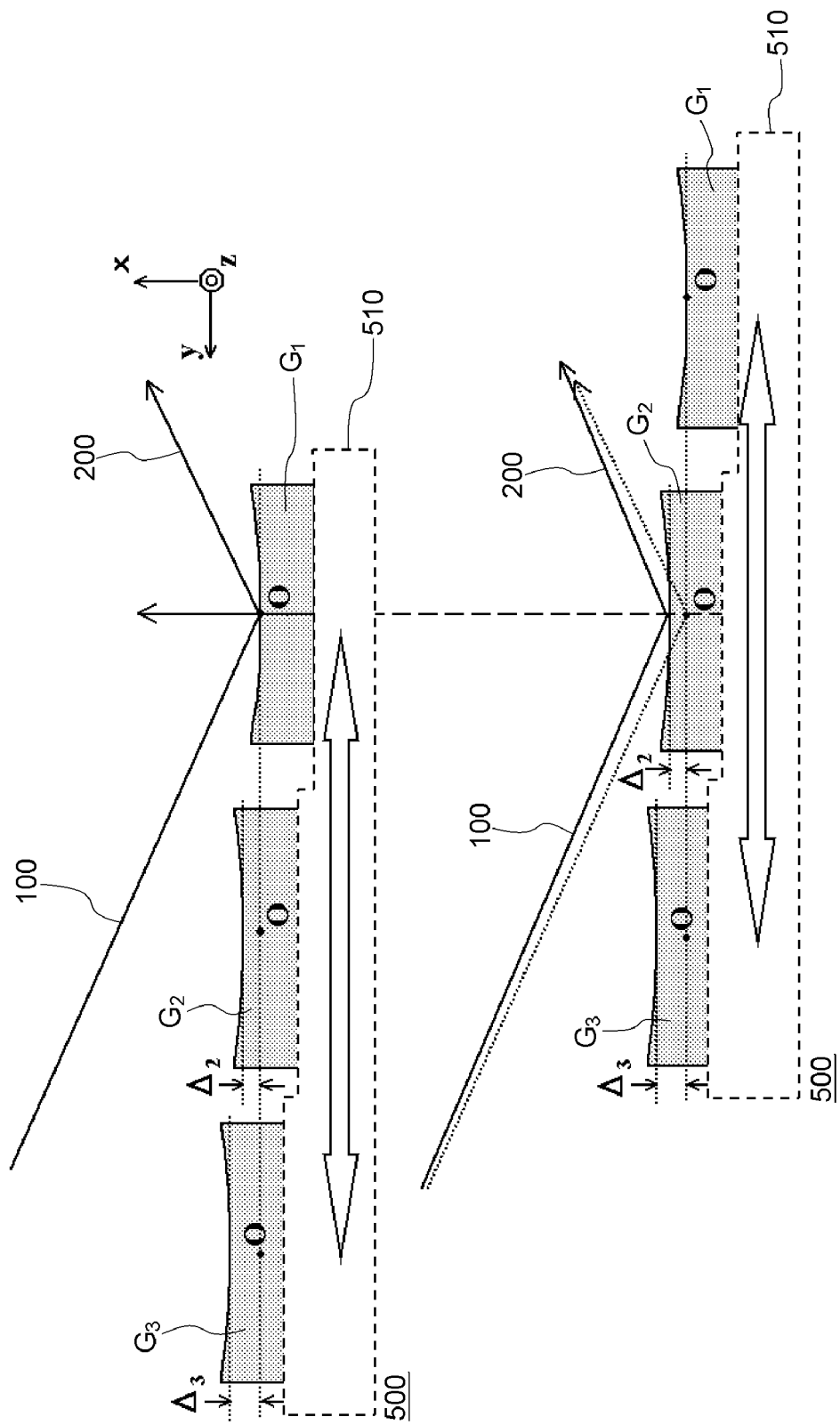
FIG. 9 gives the configuration of a first example of the spectroscopic apparatus according to an embodiment of the present invention.

FIG. 9 is a figure illustrating a configuration of a spectroscopic apparatus 500 given as a first example that translates $G_1$ to $G_3$ in the y-axis direction for making a selection. The figure at top in FIG. 9 shows a configuration in which $G_1$ is selected, while the figure at bottom a configuration in which $G_2$ is selected. It is assumed that the light source 20 is located at left in the figure in a place which is not shown, while the image plane 30 at right in the figure in a place which is not shown. In addition, the coordinate axes (x, y, z) are of the right-handed system.

In this spectroscopic apparatus 500, the VLS concave gratings $G_1$ to $G_3$ are installed, being arranged on a carriage (selection means) 510 in the horizontal direction (the y-axis direction in FIG. 1). The incident ray 100 is directed from the light source 20 to the grating, and the diffracted ray 200 is directed from the grating to the image plane 30. By moving the carriage 510 in the horizontal direction, one of the gratings $G_1$ to $G_3$ can be selected. With this configuration, the rightmost position of a particular grating provides a position where the VLS concave diffraction grating is to be used. When the respective VLS concave gratings are moved to that position, the normal line of the groove plane at the grating center thereof is treated as one which is to be superposed upon a common normal line. However, the position of the grating center in the direction of the normal line (in the x-axis direction) varies depending upon the type of VLS concave grating, being $\Delta_1$ (=0) for $G_1$, $\Delta_2$ ($\Delta_2>\Delta_1$) for $G_2$, and $\Delta_3$ ($\Delta_3>\Delta_2$) for $G_3$. As described above, with a switchover among $G_1$ to $G_3$, a changeover among $\Delta_1$ to $\Delta_3$ is caused, thereby the angle of incidence being changed over.

Figure 10:
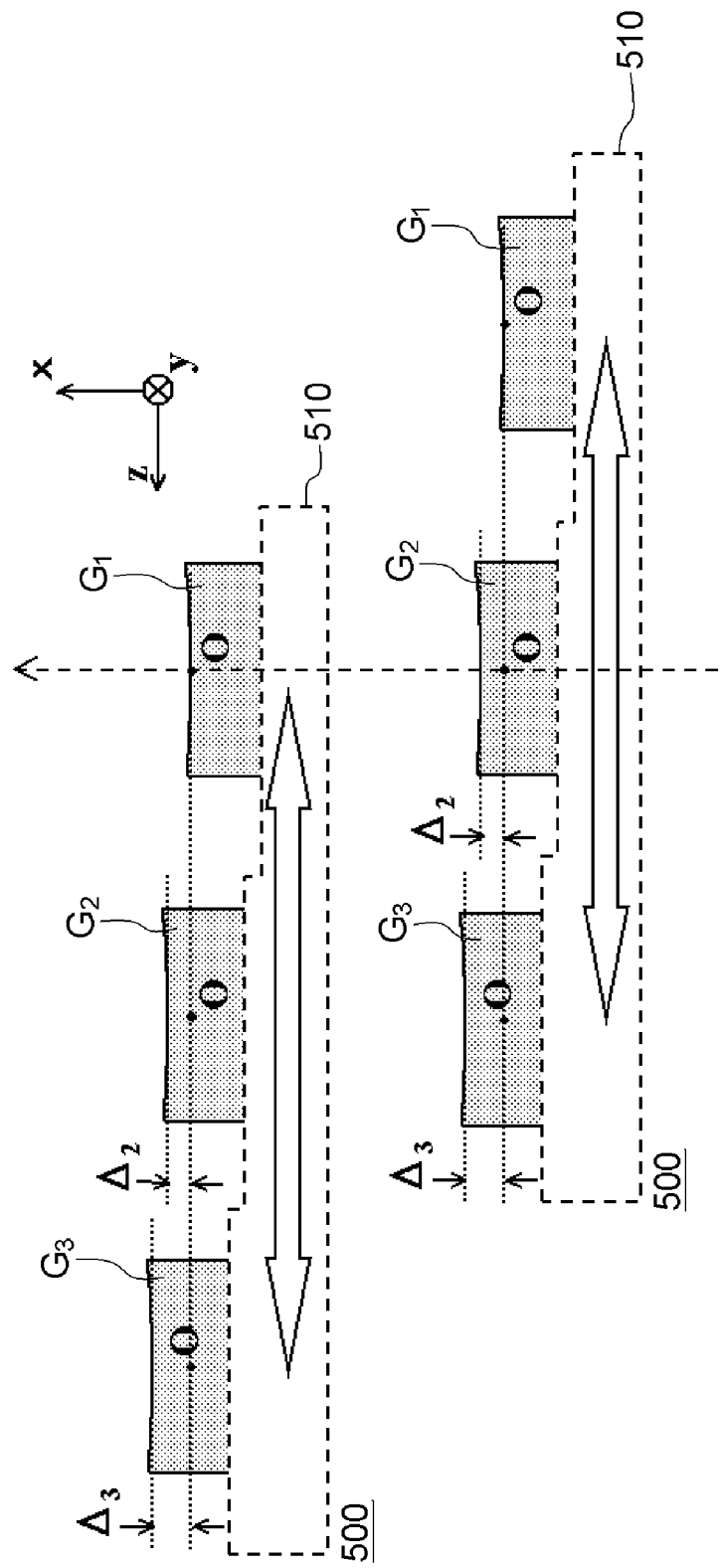
FIG. 10 gives the configuration of a modification of the first example of the spectroscopic apparatus according to an embodiment of the present invention.

With the configuration in FIG. 9, $G_1$ to $G_3$ are arranged and moved in the y-axis direction in FIG. 1, however, as shown in FIG. 10, G1 to G3 may be translated in a direction at right angles to the y-axis direction (the z-axis direction) (a modification of the first example). Here, a configuration when the incident ray side (left side) is viewed from the exit ray side (right side) in FIG. 1 is shown, and the incident ray and the diffracted ray are not shown, however, these rays are directed from the back side of the surface of the paper toward this side. In FIG. 10, the figure at top shows a configuration in which $G_1$ has been selected, while the figure at bottom shows a configuration in which $G_2$ has been selected.

In this configuration, nothing exists around the optical path except for the diffraction grating selected from among $G_1$ to $G_3$, and therefore it is easier to suppress the effect of a jig motion required for translation of $G_1$ to $G_3$, and the stray light from the adjacent VLS concave grating. Thereby, the traveling mechanism of the carriage 510 can be made compact and simple.

Figure 11:
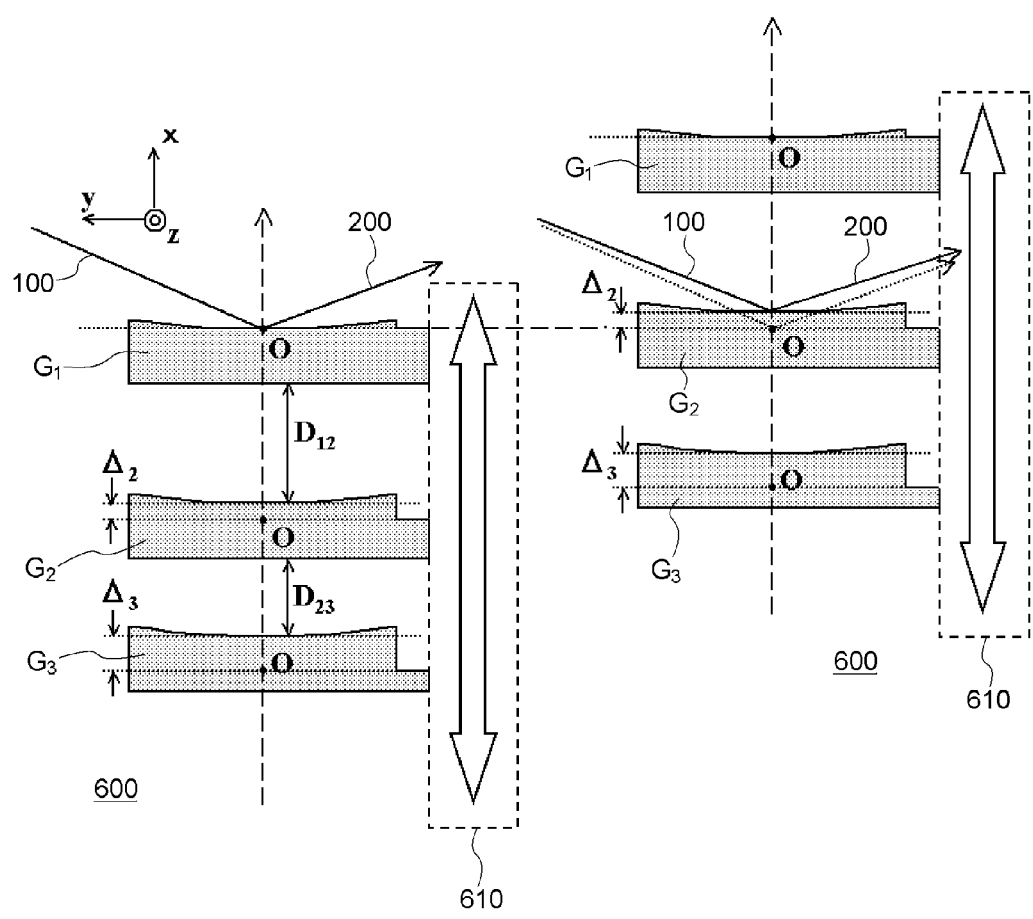
FIG. 11 gives the configuration of a second example of the spectroscopic apparatus according to an embodiment of the present invention.

FIG. 11 is a figure illustrating a configuration of a spectroscopic apparatus 600 given as a second example that moves $G_1$ to $G_3$ in the vertical direction (x-axis direction) for making a selection. In this spectroscopic apparatus 600, the VLS concave gratings $G_1$ to $G_3$ are installed, being arranged on a carriage (selection means) 610 in the vertical direction on the side faces thereof. In FIG. 11, the figure at left shows a configuration in which $G_1$ has been selected, while the figure at right shows a configuration in which $G_2$ has been selected. The incident ray 100 is directed from the light source 20 to the diffraction grating, and the diffracted ray 200 is directed from the diffraction grating to the image plane 30. By moving the carriage 610 in the x-axis direction, a switchover among $G_1$ to $G_3$ is performed. In this operation, the normal line of the groove plane at the diffraction grating center of each of $G_1$ to $G_3$ is treated as one which is to be superposed upon a common normal line, and as the position of the diffraction grating center in the direction of the normal line, $\Delta_1$ (=0) is provided for $G_1$, $\Delta_2$ ($\Delta_2 > \Delta_1$) for $G_2$, and $\Delta_3$ ($\Delta_3 > \Delta_2$) for $G_3$. As described above, with a switchover among $G_1$ to $G_3$, a changeover among $\Delta_1$ to $\Delta_3$ is caused, thereby the incident angle being changed over.

In order to provide a configuration which will minimize the possibility that the incident ray 100 and the diffracted ray 200 may be obstructed by the VLS concave grating existing just above the VLS concave grating selected ($G_1$ at left in FIG. 11, and $G_2$ at right in FIG. 11), it is recommended that $G_1$ with which the angle of incidence α is the smallest (the farthest from 90°) be located at the uppermost stage, while $G_3$ with which the angle of incidence α is the largest (the closest to 90°) be located at the lowermost stage. In this case, the spacing $D_{23}$ between the top face of the $G_3$ and the bottom face of $G_2$ can be smaller than the spacing $D_{12}$ between the top face of the $G_2$ and the bottom face of $G_1$, whereby the carriage 610 can be made compact.

Further, in the configuration as shown in FIG. 11, existence of an error of translation in the x-axis direction can directly cause an error of the incident angle for the incident ray 100, and therefore, in selecting the diffraction grating from among $G_1$ to $G_3$, it is necessary that the diffraction grating selected be accurately fixed in a predetermined position by means of a stopper. As an example thereof, in FIG. 11, a shoulder is provided at the right end of each of $G_1$ to $G_3$, and by seizing the shoulder by the lowest portion with the stopper, each of $G_1$ to $G_3$ can be fixed in a predetermined position for which Δ is taken into account.

In the case where the number of VLS concave gratings used is greater than that as is given above, and the same configuration is to be used, the VLS concave gratings are fixed using the carriage 610 such that the normal line passing through the center of the groove plane of the respective diffraction gratings is treated as one which is to be superposed upon a common normal line, and all the diffraction planes are directed upward in a uniform manner. The carriage 610 is set such that it is moved in the direction of this normal line. Further, with this laminated structure, setting the value of the maximum wavelength to be accommodated such that it is incremented in the upward direction, and incrementing the spacing between the adjacent two gratings along the vertical direction in the upward direction will allow the carriage 610 to be made compact even if more diffraction gratings are laminated.

FIG. 12 is a figure illustrating a configuration of a spectroscopic apparatus 700 given as a third example that pivots $G_1$ to $G_3$ about a pivotal movement center R for making a selection. With this spectroscopic apparatus 700, $G_1$ to $G_3$ are arranged and installed in different positions on the circumference of a turntable (selection means) 710 which pivots about an axis of pivoting that passes through the pivotal movement center R and is parallel with the z-axis in FIG. 1. In FIG. 12, the figure at top shows a configuration in which $G_1$ has been selected, while the figure at bottom shows a configuration in which $G_2$ has been selected. The incident ray 100 is directed from the light source 20 to the diffraction grating, and the diffracted ray 200 is directed from the diffraction grating to the image plane 30. By pivoting the turntable 710, a switchover among $G_1$ to $G_3$ is performed. In this operation, the normal line of the groove plane at the diffraction grating center of each of $G_1$ to $G_3$ is treated as one which is to be superposed upon a common normal line, and as the position of the diffraction grating center in the direction of the normal line, $\Delta_1$ (=0) is provided for $G_1$, $\Delta_2$ ($\Delta_2 > \Delta_1$) for $G_2$, and $\Delta_3$ ($\Delta_3 > \Delta_2$) for $G_3$, thereby with a switchover among $G_1$ to $G_3$, the incident angle being changed over.

Figure 13:
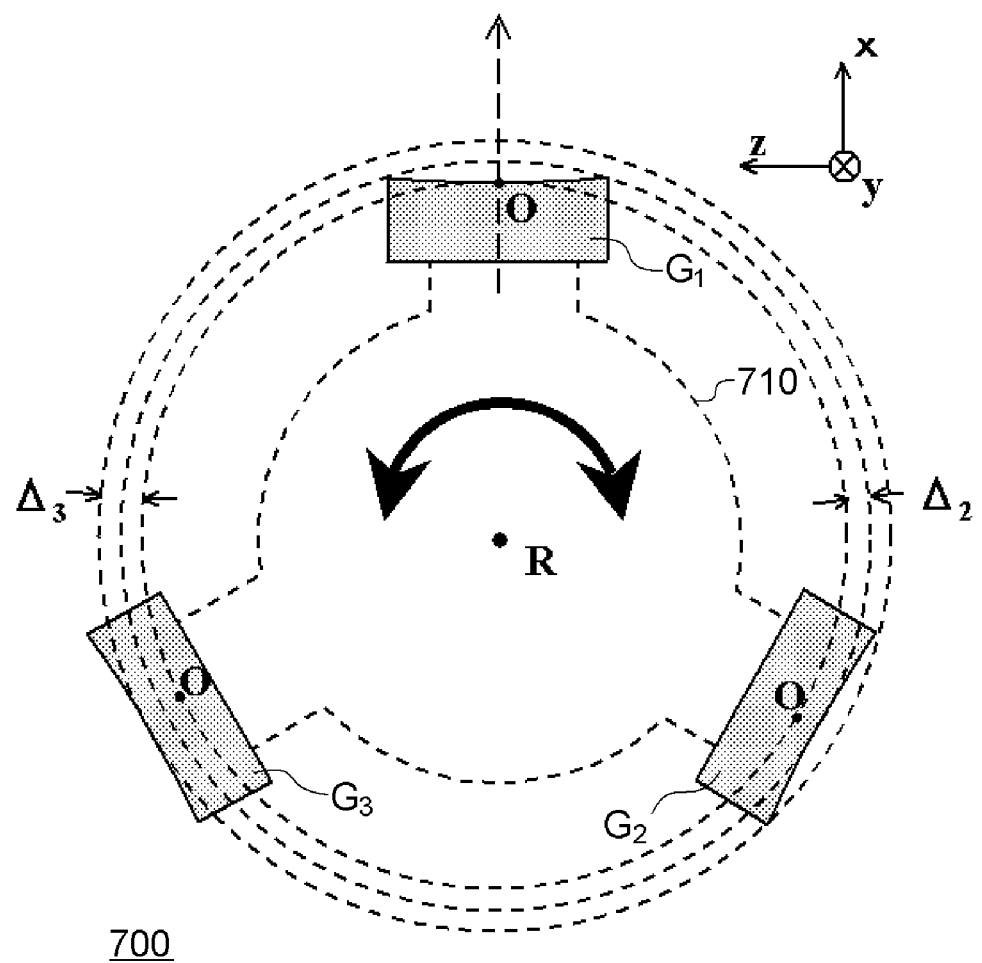
FIG. 13 gives the configuration of a modification of the third example of the spectroscopic apparatus according to an embodiment of the present invention.

Contrarily to the configuration in FIG. 12, with a configuration as shown in FIG. 13, the pivotal axis is parallel with the y-axis in FIG. 1, and around it, $G_1$ to $G_3$ are arranged (a modification of the third example). In this case, in FIG. 13, $G_1$ to $G_3$ are pivoted around the pivotal movement center R with the y-axis direction being used as the pivotal axis. With the configuration as shown in FIG. 12, existence of an error of setting the angle of pivoting can directly cause an error of the angle of incidence for the incident ray 100, while, with the configuration as shown in FIG. 13, the effect of an error of setting the angle of pivoting can be minimized. In addition, in the case where the number of VLS concave gratings which are arranged on the circumference is great, the configuration as shown in FIG. 12 may cause the optical path (the incident ray and the diffracted ray) to be affected by a diffraction grating adjacent to the diffraction grating selected, however, with the configuration as shown in FIG. 13, such effect will be reduced as is the case with the configuration in FIG. 10.

With the modification of the first example (FIG. 10), and the modification of the third example (FIG. 13), the selection means moves $G_1$ to $G_3$ within a plane provided in a direction perpendicular to the plane including the incident ray 100 and the diffracted ray 200, thereby one of them being selected. This movement is a translation one in the modification of the first example, while it is a pivotal one in the modification of the third example. With these configurations, as described above, the effect of a VLS concave grating adjacent to the VLS concave grating selected on the optical path can be reduced.

On the other hand, in the first example (FIG. 9) and the third example (FIG. 12) in which $G_1$ to $G_3$ are moved within the plane including the incident ray 100 and the diffracted ray 200, the size of the spectroscopic apparatus in a direction perpendicular to the optical path can be reduced.

In the above examples, three types of VLS concave gratings have been used for explanation, however, the number of VLS concave gratings used is optional. In addition, in the above examples, the varied space concave diffraction grating has been used, however, it is obvious that, even in the case where the grating having a planar geometry is used (in the case where R in Table 1 is equal to ∞), the same advantages can be obtained.

In addition, as the selection means, the traveling mechanism to be used in the horizontal direction (the y-axis direction or the z-axis direction), the traveling mechanism to be used in the vertical direction (the x-axis direction), the pivoting mechanism which uses an axis passing through the pivotal movement center R and parallel to the y-axis or z-axis as the pivotal axis have been explained, however, even in the case where these are combined as appropriate, or a mechanism which is different from these, the configuration of the selection means is optional, provided that the same positional relationship as that as described above is implemented in the respective VLS concave gratings.

As shown in FIG. 2, the above spectroscopic apparatus is effective regardless of the wavelength, provided that the VLS grating is used. However, the above spectroscopic apparatus is effective especially as a spectroscopic apparatus for the soft x-ray region (the wavelengths of 0.5 to 25 nm) that is used with the angle of incidence α close to 90°.

Further, the material constituting the groove plane (diffraction grating surface) of the VLS grating to be used for the soft x-ray region is optional according to the application. For example, a single layer deposited film of gold, platinum, nickel, or the like, exhibiting a high reflectivity is effective. In addition, the multi-layer film structure having a particularly high reflectivity in a specific wavelength range may be used. In that case, a spectroscopic apparatus which can cover the wavelengths shorter than 0.56 nm (the energies higher than 2200 eV) can be obtained.

What is claimed is:

1. A spectroscopic apparatus, including a plurality of varied line spacing diffraction gratings differing in range of wavelengths to be accommodated, one varied line spacing diffraction grating being selected from among the plurality of varied line spacing diffraction gratings for obtaining a desired wavelength of output light, an incident ray emitted from a light source entering the one varied line spacing diffraction grating, and a diffracted ray focusing onto an image surface common to all the varied line spacing diffraction gratings, the spectroscopic apparatus comprising a selection means for selecting the one varied line spacing diffraction grating to install it in a position where the incident ray is to be entered, wherein, in selecting the one varied line spacing diffraction grating from among the plurality of varied line spacing diffraction gratings, the selection means treats the normal line passing through the center of the groove plane of the respective varied line spacing diffraction gratings as one to be superposed upon a common normal line, and in case where the light source is on the upper side of the groove plane, selects the one varied line spacing diffraction grating and installs it such that the smaller the value of the minimum wavelength to be accommodated, the higher the position at which the groove plane is set.

2. The spectroscopic apparatus according to claim 1, wherein the light source emits light having a wavelength in the range of 0.5 to 25 nm.

3. The spectroscopic apparatus according to claim 1, wherein the groove plane of the varied line spacing diffraction grating is provided with a concave geometry.

4. The spectroscopic apparatus according to claim 1, wherein a groove in the varied line spacing diffraction grating has been formed by using an aspherical wavefront holographic recoding method.

5. The spectroscopic apparatus according to claim 1, wherein a multi-layer film has been formed on the groove plane in the varied line spacing diffraction grating.

6. The spectroscopic apparatus according to claim 1, wherein the selection means selects the one varied line spacing diffraction grating by translating or pivoting the plurality of varied line spacing diffraction gratings to a position where the normal line passing through the center of the groove plane of the one varied line spacing diffraction grating is superposed upon the common normal line.

* * * * *